United States Patent
Trigg et al.

(10) Patent No.: US 9,951,011 B2
(45) Date of Patent: *Apr. 24, 2018

(54) CARBAZOLE COMPOUNDS FOR IN VIVO IMAGING

(71) Applicant: GE Healthcare Limited, Buckinghamshire (GB)

(72) Inventors: William John Trigg, Little Chalfont (GB); Paul Alexander Jones, Little Chalfont (GB)

(73) Assignee: GE HEALTHCARE LIMITED (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/917,707

(22) PCT Filed: Sep. 19, 2014

(86) PCT No.: PCT/EP2014/069969
§ 371 (c)(1),
(2) Date: Mar. 9, 2016

(87) PCT Pub. No.: WO2015/040148
PCT Pub. Date: Mar. 26, 2015

(65) Prior Publication Data
US 2016/0214936 A1    Jul. 28, 2016

(30) Foreign Application Priority Data

Sep. 20, 2013 (GB) .................................. 1316762.2

(51) Int. Cl.
*A61K 51/00* (2006.01)
*A61K 36/14* (2006.01)
*C07D 209/88* (2006.01)
*A61K 51/04* (2006.01)

(52) U.S. Cl.
CPC ........ *C07D 209/88* (2013.01); *A61K 51/0446* (2013.01)

(58) Field of Classification Search
CPC .................................................... A61K 51/00
See application file for complete search history.

(56) References Cited

U.S. PATENT DOCUMENTS

2011/0070161 A1* 3/2011 Achanath ........... A61K 51/0446
                                                         424/1.89
2012/0020884 A1* 1/2012 Wadsworth ........ A61K 51/0446
                                                         424/1.89

FOREIGN PATENT DOCUMENTS

WO    2010/109007 A2    9/2010
WO    2012/038532 A1    3/2012
WO    2012/041953 A1    4/2012

OTHER PUBLICATIONS

Jason R. Buck et al. Quantitative, Preclinical PET of Translocator Protein Expression in Glioma Using 18F-N-Fluoroacetyl-N-(2,5-Dimethoxybenyl)-2-Phenoxyaniline, J. Nucl. Med. 2011, 52, 107-114).*
International Search Report and Written Opinion Regarding International Application No. PCT/EP2014/069969, dated Nov. 19, 2014, 12 pages.
Wadsworth et al., "[18F] GE-180: A Novel Fluorine-18 labelled PET tracer for imaging Translocator protein 18kDa (TSPO)", Bioorganic & Medicinal Chemistry Letters, vol. 22, No. 3, Feb. 1, 2012, pp. 1308-1313.
Search Report Regarding GB Application No. 1316762.2, dated Mar. 10, 2014, 5 pages.

* cited by examiner

*Primary Examiner* — Michael G Hartley
*Assistant Examiner* — Jagadishwar R Samala
(74) *Attorney, Agent, or Firm* — Wood IP LLC

(57) ABSTRACT

The present invention concerns in vivo imaging and in particular in vivo imaging of translocator protein (TSPO, formerly known as the peripheral benzodiazepine receptor). An indole-based in vivo imaging agent is provided that overcomes problems relating to known TSPO-binding radiotracers. The present invention also provides a precursor compound useful in the synthesis of the in vivo imaging agent of the invention, as well as a method for synthesis of said precursor compound. Other aspects of the invention include a method for the synthesis of the in vivo imaging agent of the invention comprising use of the precursor compound of the invention, a kit for carrying out said method, and a cassette for carrying out an automated version of said method. In addition, the invention provides a radiopharmaceutical composition comprising the in vivo imaging agent of the invention, as well as methods for the use of said in vivo imaging agent.

13 Claims, No Drawings

1

CARBAZOLE COMPOUNDS FOR IN VIVO IMAGING

CROSS-REFERENCE TO RELATED APPLICATIONS

This application is a filing under 35 U.S.C. 371 of international application number PCT/EP2014/069969, filed Sep. 19, 2014, which claims priority to Great Britain application number GB 1316762.2, filed Sep. 20, 2013, the entire disclosures of each of which are hereby incorporated by reference.

TECHNICAL FIELD OF THE INVENTION

The present invention concerns in vivo imaging and in particular in vivo imaging of translocator protein (TSPO, formerly known as the peripheral benzodiazepine receptor). An indole-based in vivo imaging agent is provided that overcomes problems relating to known TSPO-binding radiotracers. The present invention also provides a precursor compound useful in the synthesis of the in vivo imaging agent of the invention, as well as a method for synthesis of said precursor compound. Other aspects of the invention include a method for the synthesis of the in vivo imaging agent of the invention comprising use of the precursor compound of the invention, a kit for carrying out said method, and a cassette for carrying out an automated version of said method. In addition, the invention provides a radiopharmaceutical composition comprising the in vivo imaging agent of the invention, as well as methods for the use of said in vivo imaging agent.

DESCRIPTION OF RELATED ART

TSPO is known to be mainly localised in peripheral tissues and glial cells but its physiological function remains to be clearly elucidated. Subcellularly, TSPO is known to localise on the outer mitochondrial membrane, indicating a potential role in the modulation of mitochondrial function and in the immune system. It has furthermore been postulated that TSPO is involved in cell proliferation, steroidogenesis, calcium flow and cellular respiration.

In studies examining the expression of TSPO in normal and diseased tissue, Cosenza-Nashat et al (2009 Neuropathol Appl Neurobiol; 35(3): 306-328) confirmed that TSPO expression in normal brain is minimal. This same paper demonstrated that in disease states elevated TSPO was present in parenchymal microglia, macrophages and some hypertrophic astrocytes, but the distribution of TSPO varied depending on the disease, disease stage and proximity to the lesion or relation to infection. Microglia and macrophages are the predominant cell type expressing TSPO in diseased brains, and astrocytes can also express TSPO in humans.

Positron emission tomography (PET) imaging using the TSPO selective ligand, (R)-[$^{11}$C]PK11195 has been widely used as a generic indicator of central nervous system (CNS) inflammation. However, there are numerous limitations with (R)-[$^{11}$C]PK11195 as a TSPO imaging agent, including high nonspecific binding, low brain penetration, high plasma protein binding, and a difficult synthesis. Furthermore, the role of its radiolabelled metabolites is not known, and quantification of binding requires complex modelling.

Prompted by the issues with (R)-[$^{11}$C]K11195, a next generation of TSPO-binding PET tracers has been developed leading to some demonstrating higher specific to non-specific signals and higher brain uptake, including [$^{18}$F]-FEPPA, [$^{18}$F] PBR111, [$^{11}$C]-PBR28, [$^{11}$C]-DPA713, [$^{11}$C]-DAA1106, and [$^{11}$C]-AC-5126 (Chauveau et al 2008 Eur J Nucl Med Mol Imaging; 35: 2304-2319). However, more recently, intra-subject variability in PET results has been observed in this new generation of tracers. These tracers bind TSPO in brain tissue from different subjects in one of three ways. High-affinity binders (HABs) and low-affinity binders (LABs) express a single binding site for TSPO with either high or low affinity, respectively. Mixed affinity binders (MABs) express roughly equal numbers of the HAB and LAB binding sites (Owen et al 2011 J Nucl Med; 52: 24-32). Owen et al (J Cerebral Blood Flow Metab 2012; 32:1-5) demonstrated that a polymorphism in TSPO (Ala147Thr) is responsible for the observed intra-subject variability in binding.

Fujita et al (Neuroimage 2008; 40: 43-52) carried out [$^{11}$C]PBR28 imaging in healthy volunteers and noted that 2 out of the 12 subjects imaged had a time course of brain activity that could have been mimicked by the absence or blockade of TSPO. Whole body imaging of these 2 subjects showed negligible binding to kidneys, lungs and spleen so that they appeared to lack the binding site of [$^{11}$C]PBR28 or lack TSPO receptors.

In another study examining in vivo imaging of [$^{11}$C] PBR28 (Kreisl et al NeuroImage 2010; 49: 2924-2932), uptake in organs with high densities of TSPO was shown to be 50% to 75% lower in LABs than in HABs, whereas for [$^{11}$C]PK11195 differences in uptake were only seen in heart and lung. [$^{3}$H]PBR28 in an in vitro assay showed more than 10-fold lower TSPO affinity in LABs than in HABs. In monkeys, in vivo specific binding of [$^{11}$C]PK11195 in monkey brain was ~80-fold lower than that reported for [$^{11}$C]PBR28. These results supported a conclusion that non-binding of [$^{11}$C]PBR28 in LABs was due to low affinity for TSPO, and that the relatively low in vivo specific binding of [$^{11}$C]PK11195 may have obscured its detection of non-binding in peripheral organs.

Mizrahi et al (2012 J Cerebral Blood Flow Metabol; 32: 968-972) demonstrated that [$^{18}$F]FEPPA demonstrates clear differences in the in vivo imaging characteristics between binding groups.

The presence HABs, MABs and LABs presents a problem for the utility of TSPO radioligands because the signal cannot reliably be interpreted. It would be desirable to develop a strategy that overcomes this problem.

SUMMARY OF THE INVENTION

The present invention provides compounds that bind to TSPO and have improved binding properties compared with known compounds. In particular, the compounds of the present invention address the issue of heterogenous binding in HABs, MABs and LABs.

DESCRIPTION OF THE PREFERRED EMBODIMENTS

In one aspect, the present invention provides a compound of Formula I:

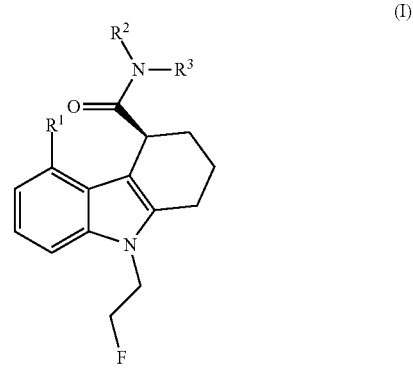

(I)

wherein:

R¹ is hydrogen or methoxy; and,

R² is ethyl and R³ is benzyl, or R² is methyl and R³ is isopropyl.

The term "methoxy" refers to the substituent —O—CH₃.

The term "ethyl" refers to the substituent —CH₂—CH₃.

The term "benzyl" refers to the substituent —CH₂-phenyl.

The term "methyl" refers to the substituent —CH₃.

The term "isopropyl" refers to the substituent —CH₂(CH₃)₂.

In one preferred embodiment of Formula I R¹ is methoxy.

In an alternative preferred embodiment of Formula I R¹ is hydrogen.

In one preferred embodiment of Formula I R² is ethyl and R³ is benzyl.

In an alternative preferred embodiment of Formula I R² is methyl and R³ is isopropyl.

Preferred compounds of Formula I are as follows:

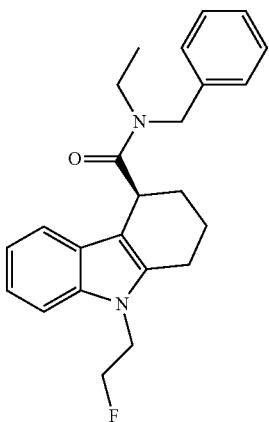

1

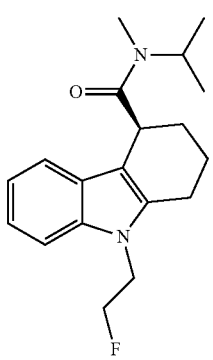

2

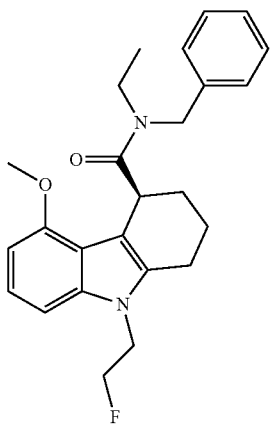

3

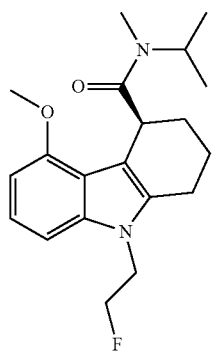

4

In another aspect, the present invention provides a precursor compound for use in the preparation of the compound of Formula I as defined herein, wherein said precursor compound is of Formula II:

(II)

wherein R¹¹, R¹² and R¹³ are as defined for R¹, R² and R³ hereinabove, including preferred embodiments, and LG is a leaving group.

A "leaving group" in the context of the present invention refers to an atom or group of atoms that is displaced as a stable species during a substitution or displacement radiofluorination reaction. Examples of suitable leaving groups are the halogens chloro, bromo and iodo, and the sulfonate esters mesylate, tosylate nosylate and triflate. In one embodiment, said leaving group is selected from mesylate, tosylate and triflate, and is preferably mesylate.

Scheme 1 below is a generic reaction scheme that shows how to obtain compounds that can themselves be precursor compounds of the invention, or that can be converted into precursor compounds (or different precursor compounds) with a small number of facile further steps. $R^{11-14}$ and $Y^{11-12}$ of Scheme 1 are as defined above for Formula II.
Scheme 1
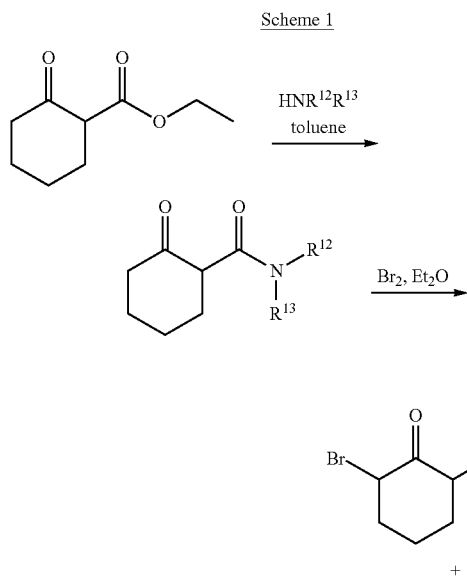
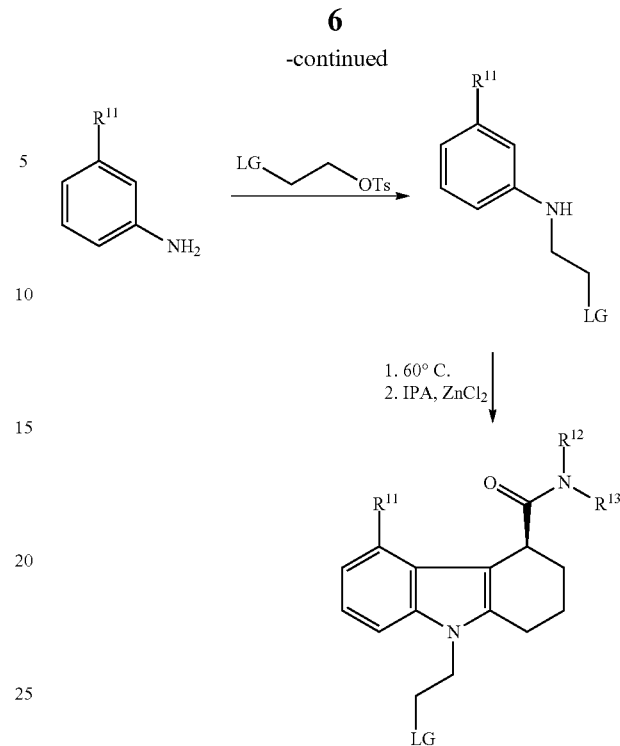
Alternatively, the general synthetic route illustrated in Scheme 1a below can be used:
Scheme 1a
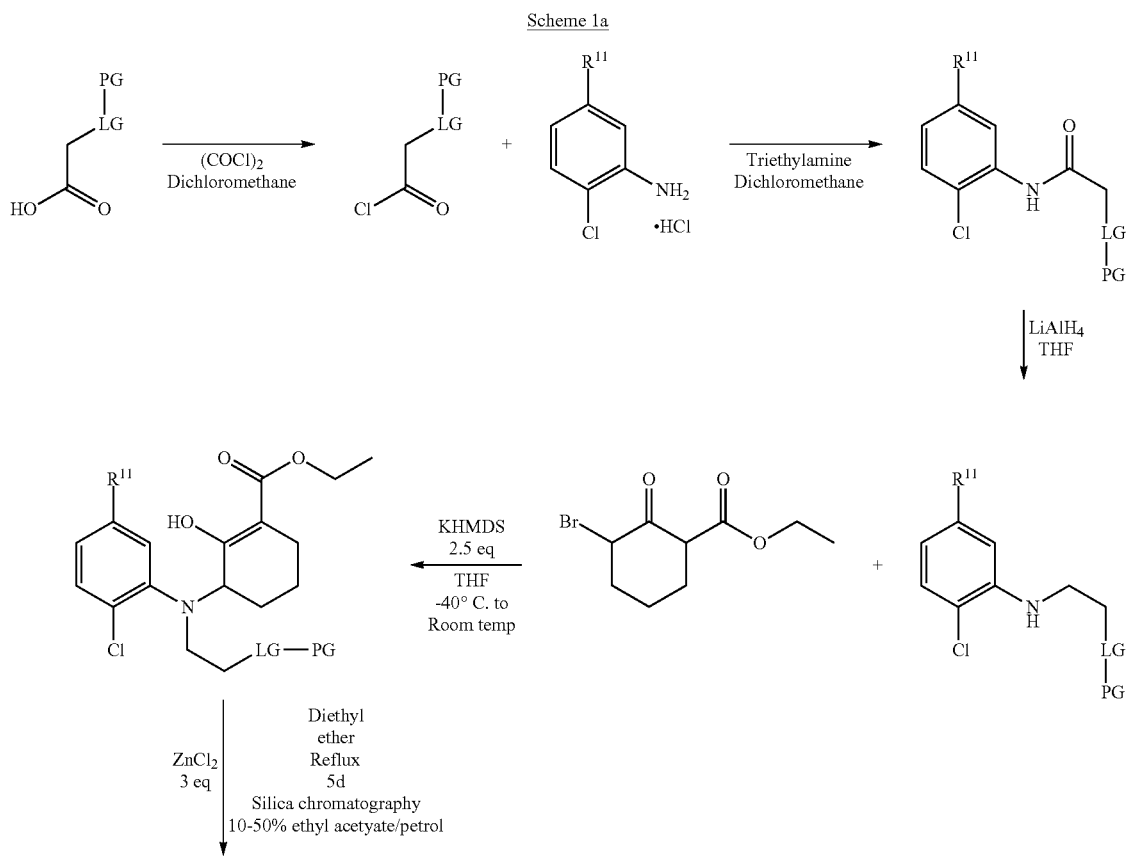

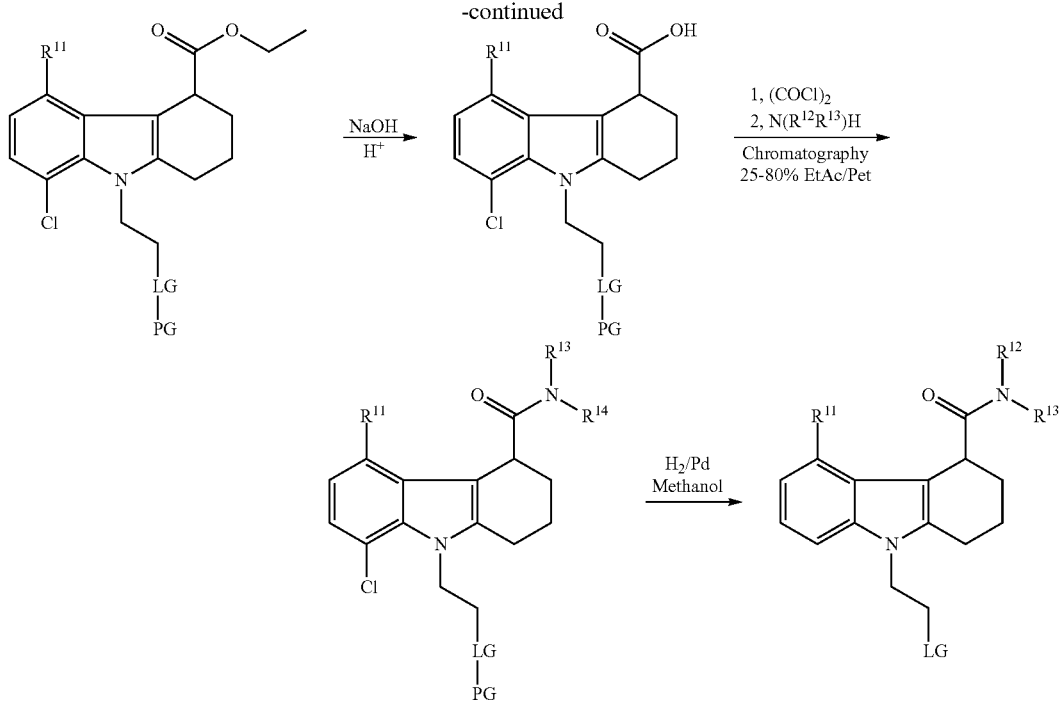

In Scheme 1a above, -LG-PG represents a protected leaving group. $R^{11-13}$ are as suitably and preferably provided for Formula II above. In this synthetic route, the chlorine at the bottom position on the ring forces the cyclisation to take place in just one way such that only one isomer is produced. A similar method is disclosed in WO 2003/014082. However, when the teachings of WO 2003/014082 were used to obtain precursor compounds similar to those of the present invention, the yield was low. This problem was overcome by changing the solvent system used for the cyclisation step. In WO 2003/014082 the cyclisation step is carried out in toluene, whereas the present inventors found that optimum yields were obtained when diethyl ether was used in place of toluene. The product of the cyclisation step dissolves in diethyl ether whereas the uncyclised starting compound does not. The uncyclised starting compound therefore remains with the $ZnCl_2$ at the bottom of the reaction vessel, and the cyclised product moves into the diethyl ether at the top of the reaction vessel.

In a further aspect, the present invention provides a method to prepare the compound of Formula I as defined herein wherein said method comprises reacting the precursor compound of Formula II as defined herein with a suitable source of [$^{18}$F]fluoride to obtain said compound of Formula I.

The term "suitable source of [$^{18}$F]fluoride" means [$^{18}$F] fluoride in a chemical form that replaces LG in a nucleophilic substitution reaction. [$^{18}$F]-fluoride ion ($^{18}$F) is normally obtained as an aqueous solution from the nuclear reaction $^{18}$O(p,n)$^{18}$F and typically made reactive by the addition of a cationic counterion and the subsequent removal of water.

Suitable cationic counterions should possess sufficient solubility within the anhydrous reaction solvent to maintain the solubility of [$^{18}$F]fluoride. Counterions that are typically used include large but soft metal ions such as rubidium or caesium, potassium complexed with a cryptand such as Kryptofix™ 2.2.2 (K222), or tetraalkylammonium salts. A preferred counterion is potassium complexed with a cryptand such as K222 because of its good solubility in anhydrous solvents and enhanced [$^{18}$F]fluoride reactivity.

A more detailed discussion of well-known $^{18}$F labelling techniques can be found in Chapter 6 of the "Handbook of Radiopharmaceuticals" (2003; John Wiley and Sons: M. J. Welch and C. S. Redvanly, Eds.).

In a preferred embodiment, the method to prepare a compound of Formula I of the invention is automated. [18F]-radiotracers may be conveniently prepared in an automated fashion by means of an automated radiosynthesis apparatus. There are several commercially-available examples of such apparatus, including Tracerlab MX™ and FASTlab™ (GE Healthcare), FDGPlus Synthesizer (Bioscan) and Synthera® (IBA). Such apparatus commonly comprises a "cassette" (sometimes referred to as a "cartridge"), often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

The present invention provides in another aspect a cassette for carrying out the automated method of the invention wherein said cassette comprises:
  (i) a vessel containing the precursor compound of Formula II as defined herein; and,
  (ii) means for eluting the vessel of step (i) with a suitable source of [$^{18}$F]fluoride.

The cassette of the invention optionally also comprises:
  (iii) an ion-exchange cartridge for removal of excess [$^{18}$F]fluoride; and/or
  (iv) one or more solid phase extraction cartridges for purification of the [$^{18}$F] labelled reaction mixture.

For the cassette of the invention, the suitable and preferred embodiments of the precursor compound of Formula II and suitable source of [$^{18}$F]fluoride are as previously defined herein.

Another aspect of the invention is a radiopharmaceutical composition comprising the compound of Formula I as defined herein together with a biocompatible carrier in a form suitable for mammalian administration. The "biocompatible carrier" is a fluid, especially a liquid, in which the compound of Formula I is suspended or dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The pH of the biocompatible carrier for intravenous injection is suitably in the range 4.0 to 10.5.

The pharmaceutical composition may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ethanol, ascorbic acid, gentisic acid or para-aminobenzoic acid).

The radiopharmaceutical composition may be administered parenterally, i.e. by injection. Where the compound of Formula I is provided as a radiopharmaceutical composition, the method for preparation of said compound suitably further comprises steps including removal of organic solvent, addition of a biocompatible buffer and any optional further ingredients. For parenteral administration, steps to ensure that the radiopharmaceutical composition is sterile and apyrogenic also need to be taken.

For the radiopharmaceutical composition of the invention, the suitable and preferred embodiments of the compound of Formula I are as defined earlier in the specification.

The compound of Formula I of the present invention has good binding affinity for TSPO. Therefore in a further aspect, the present invention provides an in vivo imaging method for determining the distribution and/or the extent of TSPO expression in a subject wherein said method comprises:
(i) administering to said subject a compound of Formula I as defined herein;
(ii) allowing said compound to bind to TSPO expressed in said subject;
(iii) detecting signals emitted by the radioisotope of said compound using positron-emission tomography (PET);
(iv) generating an image representative of the location and/or amount of said signals; and,
(v) determining the distribution and extent of TSPO expression in said subject wherein said expression is directly correlated with said signals emitted by said compound.

"Administering" the compound of Formula I is preferably carried out parenterally, and most preferably intravenously. The intravenous route represents the most efficient way to deliver the in vivo imaging agent throughout the body of the subject and therefore into contact with TSPO expressed in said subject. Furthermore, intravenous administration does not represent a substantial physical intervention or a substantial health risk. The compound of Formula I of the invention is preferably administered as the pharmaceutical composition of the invention, as defined herein. The in vivo imaging method of the invention can also be understood as comprising the above-defined steps (ii)-(v) carried out on a subject to whom the in vivo imaging agent of the invention has been pre-administered.

Following the administering step and preceding the detecting step, the compound of Formula I is allowed to bind to TSPO. For example, when the subject is an intact mammal, the compound of Formula I will dynamically move through the mammal's body, coming into contact with various tissues therein. Once the compound of Formula I comes into contact with TSPO, a specific interaction takes place such that clearance of the compound of Formula I from tissue with TSPO takes longer than from tissue without, or with less TSPO. A certain point in time will be reached when detection of compound of Formula I specifically bound to TSPO is enabled as a result of the ratio between compound of Formula I bound to tissue with TSPO versus that bound in tissue without, or with less TSPO. An ideal such ratio is around 2:1.

The "detecting" step of the method of the invention involves detection of signals emitted by the radioisotope by means of a detector sensitive to said signals. This detection step can also be understood as the acquisition of signal data. Positron-emission tomography (PET) is a suitable in vivo imaging procedure for use in the method of the invention.

The "generating" step of the method of the invention is carried out by a computer which applies a reconstruction algorithm to the acquired signal data to yield a dataset. This dataset is then manipulated to generate images showing the location and/or amount of signals emitted by said radioisotope. The signals emitted directly correlate with the expression of TSPO such that the "determining" step can be made by evaluating the generated image.

The "subject" of the invention can be any human or animal subject. Preferably the subject of the invention is a mammal. Most preferably, said subject is an intact mammalian body in vivo. In an especially preferred embodiment, the subject of the invention is a human. The in vivo imaging method may be used to study TSPO in healthy subjects, or in subjects known or suspected to have a pathological condition associated with abnormal expression of TSPO (hereunder a "TSPO condition"). Preferably, said method relates to the in vivo imaging of a subject known or suspected to have a TSPO condition, and therefore has utility in a method for the diagnosis of said condition.

Examples of such TSPO conditions where in vivo imaging would be of use include multiple sclerosis, Rasmeussen's encephalitis, cerebral vasculitis, herpes encephalitis, AIDS-associated dementia, Parkinson's disease, corticobasal degeneration, progressive supranuclear palsy, multiple system atrophy, Huntington's Disease, amyotrophic lateral sclerosis, Alzheimer's disease, ischemic stroke, peripheral nerve injury, epilepsy, traumatic brain injury, acute stress, chronic stress, neuropathic pain, lung inflammation, chronic obstructive pulmonary disease, asthma, inflammatory bowel disease, rheumatoid arthritis, primary fibromyalgia, nerve injury, atherosclerosis, kidney inflammation, ischemia-reperfusion injury, and cancer, in particular cancer of the colon, prostate or breast. The compounds of Formula I of the invention are particularly suited to in vivo imaging of the CNS due to their good brain uptake.

In an alternative embodiment, the in vivo imaging method of the invention may be carried out repeatedly during the course of a treatment regimen for said subject, said regimen comprising administration of a drug to combat a TSPO condition. For example, the in vivo imaging method of the invention can be carried out before, during and after treatment with a drug to combat a TSPO condition. In this way, the effect of said treatment can be monitored over time. PET has excellent sensitivity and resolution, so that even relatively small changes in a lesion can be observed over time, which is particularly advantageous for treatment monitoring.

In an alternative aspect, the present invention provides said compound of Formula I for use in an in vivo imaging method as defined herein.

In another alternative aspect, the present invention provides the compound of Formula I as defined herein for use in the manufacture of a radiopharmaceutical composition as defined herein for use in an in vivo imaging method as defined herein.

In a yet further aspect, the present invention provides a method for diagnosis of a condition in which TSPO is upregulated, said method comprising the in vivo imaging method as defined herein, together with a further step (vi) of attributing the distribution and extent of TSPO expression to a particular clinical picture.

In an alternative aspect, the present invention provides the compound of Formula I as defined herein for use in the method for diagnosis as defined herein.

In another alternative aspect, the present invention provides the compound of Formula I as defined herein for use in the manufacture of a radiopharmaceutical composition as defined herein for use in the method for diagnosis as defined herein.

The invention is now illustrated by a series of non-limiting examples.

BRIEF DESCRIPTION OF THE EXAMPLES

Example 1 describes the prior art compounds used to compare with compounds of the present invention.

Example 2 describes the synthesis of (S)—N-benzyl-N-ethyl-9-(2-fluoroethyl)-2,3,4,9-tetrahydro-1H-carbazole-4-carboxamide (non-radioactive Compound 1 of the invention).

Example 3 describes the synthesis of (S)—N-isopropyl-N-methyl-9-(2-fluoroethyl)-2,3,4,9-tetrahydro-1H-carbazole-4-carboxamide (non-radioactive Compound 2 of the invention).

Example 4 describes the synthesis of (S)—N-benzyl-N-ethyl-9-(2-fluoroethyl)-5-methoxy-2,3,4,9-tetrahydro-1H-carbazole-4-carboxamide (non-radioactive Compound 3 of the invention).

Example 5 describes the synthesis of (S)—N-methyl-N-isopropyl-9-(2-fluoroethyl)-5-methoxy-2,3,4,9-tetrahydro-1H-carbazole-4-carboxamide (non-radioactive Compound 4 of the invention).

Example 6 describes the testing of racemates in the binder/non-binder assay.

Example 7 describes the testing of resolved enantiomers in the binder/non-binder assay.

LIST OF ABBREVIATIONS USED IN THE EXAMPLES

DMF dimethylformamide
h hour(s)
min minute(s)
NMR nuclear magnetic resonance
PEI polyetherimide
SFC supercritical fluid chromatography
Temp temperature
THF tetrahydrofuran

EXAMPLES

Example 1: Prior Art Compounds

Example 1(i): PK11195

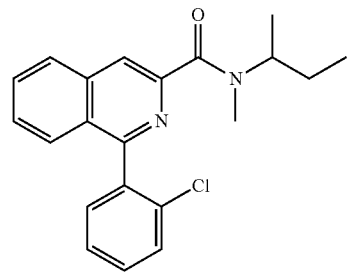 [SMILES: CCC(C)N(C)C(=O)c1cc2ccccc2c(-c2ccccc2Cl)n1]

PK11195 is commercially available.

Example 1(ii): N-(2-methoxybenzyl)-N-(4-phenoxy-pyridin-3-yl)acetamide (PBR28)

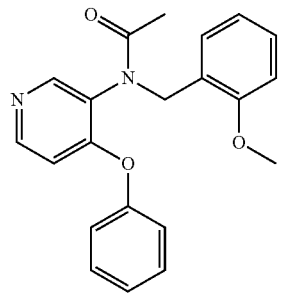 [SMILES: COc1ccccc1CN(C(C)=O)c1cnccc1Oc1ccccc1]

Non-radioactive PBR28 is commercially available.

Example 1(iii): Non-Radioactive 9-(2-Fluoro-ethyl)-5-methoxy-2,3,4,9-tetrahydro-1H-carbazole-4-carboxylic acid diethylamide (Known as "GE180")

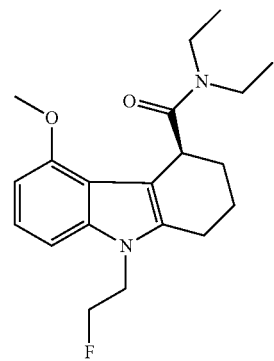 [SMILES: CCN(CC)C(=O)[C@H]1CCCc2c1c1c(OC)cccc1n2CCF]

A non-radioactive version of the prior art compound 9-(2-Fluoro-ethyl)-5-methoxy-2,3,4,9-tetrahydro-1H-carbazole-4-carboxylic acid diethylamide (known as "GE180") was prepared according to the method described by Wadsworth et al (2012 Bioorg Med Chem Letts; 22: 1308-1313) and in Examples 2 and 14 of WO 2010/109007.

Example 2: Synthesis of (S)—N-benzyl-N-ethyl-9-(2-fluoroethyl)-2,3,4,9-tetrahydro-1H-carbazole-4-carboxamide (Non-Radioactive Compound 1 of the Invention)

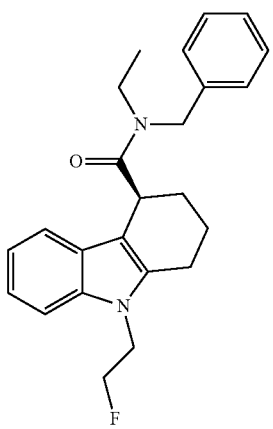 [SMILES: CCN(Cc1ccccc1)C(=O)[C@H]1CCCc2c1c1ccccc1n2CCF]

The racemate was synthesised as described by Wadsworth et al (2012 Bioorg Med Chem Letts; 22: 1308-1313).

SFC chiral separation was used to separate out the S-enantiomer using the following conditions:

$CO_2$: AGA SFC grade
Column: Whelk-01 10 × 250 mm, 5 μm, 100 Å
Flow: 13 ml/min
Pressure: 100 bar
Temp: 40° C.
Eluent: 40% Methanol
Injection concentration: 144 mg/ml
Injection solvent: Dioxane
Injection volume: 100 μL
S-enantiomer: Retention time: 3.3 min, purity 98%
R-enantiomer: Retention time: 7.4 min, purity 100%

Example 3: Synthesis of (S)—N-isopropyl-N-methyl-9-(2-fluoroethyl)-2,3,4,9-tetrahydro-1H-carbazole-4-carboxamide (Non-Radioactive Compound 2 of the Invention)

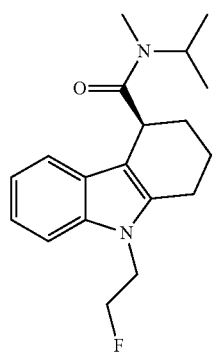 [SMILES: CC(C)N(C)C(=O)[C@H]1CCCc2c1c1ccccc1n2CCF]

The racemate was synthesised as described by Wadsworth et al (2012 Bioorg Med Chem Letts; 22: 1308-1313).

SFC chiral separation was used to separate out the S-enantiomer using the following conditions:

$CO_2$: AGA SFC grade
Column: Whelk-01 10 × 250 mm, 5 μm, 100 Å, type S,S
Flow: 13 ml/min
Pressure: 100 bar
Temp: 40° C.
Eluent: 35% Methanol
Injection concentration: 85 mg/ml
Injection solvent: MeCN
Injection volume: 100 μL
S-enantiomer: Retention time: 3.5 min, purity 99%
R-enantiomer: Retention time: 7.2 min, purity 99%

Example 4: Synthesis of (S)—N-benzyl-N-ethyl-9-(2-fluoroethyl)-5-methoxy-2,3,4,9-tetrahydro-1H-carbazole-4-carboxamide (Non-Radioactive Compound 3 of the Invention)

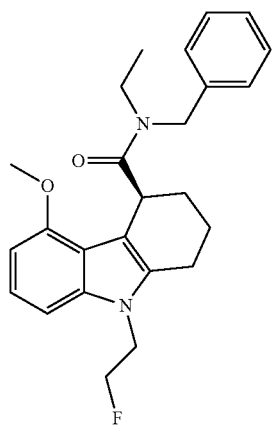 [SMILES: CCN(Cc1ccccc1)C(=O)[C@H]1CCCc2c1c1c(OC)cccc1n2CCF]

Example 4(i):
N-(2-chloro-5-methoxyphenyl)-2-fluoroacetamide

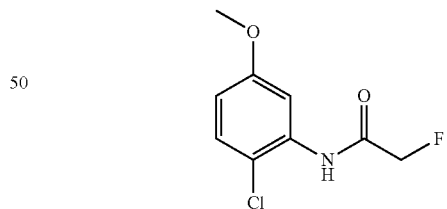

A solution of fluoroacetyl chloride (3 g, 31.1 mmol) was added dropwise to an ice cold solution of 2-chloro-5-methoxyaniline (5 g, 31.7 mmol) and triethylamine (4.5 ml, 32.3 mmol) in dichloromethane (20 ml) and left stirring overnight. Water (50 ml) was added and the biphasic mixture was stirred for 2 minutes and then separated.

The aqueous phase was extracted with dichloromethane (20 ml) and the combined organic phases were dried over magnesium sulfate (5 g). After evaporation the crude solid material was used in the next step.

Example 4(ii):
2-chloro-N-(2-fluoroethyl)-5-methoxyaniline

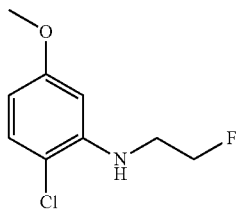

A dry flask under argon fitted with dropping funnel and a thermometer was charged with N-(2-chloro-5-methoxyphenyl)-2-fluoroacetamide (5.48 g, 25.2 mmol), THF (100 ml) and sodium borohydride (2.288 g, 60.5 mmol). A solution of iodine (6.40 g, 25.2 mmol) in THF (13 ml) was added over two hours while keeping the temperature below 30° C. The reaction mixture was stirred overnight at ambient temp and the following day the temperature was raised to 40° C. for 3 h. After filtration the mixture was quenched with 10% hydrochloric acid (10 ml) to pH 2 followed by 10% sodium hydroxide (10 ml) while keeping the temperature below 30° C. Water (200 ml) was added and the mixture was evaporated to remove THF. The aqueous phase was extracted twice with dichloromethane (50 ml) and the organic phase was washed once with water, dried over magnesium sulfate (5 g) and evaporated to yield a clear oil. The crude product was purified on silica (5.5×16 cm) with dichloromethane, 3.86 g of the title compound was obtained.

$^1$H NMR, 400 MHz (CDCl$_3$, 25° C.): 7.20 ppm (d, 1H, J=8.7 Hz), 6.40 ppm (d, 1H, J=2.8 Hz), 6.33 ppm (dd, 1H, J=8.7 Hz, 2.8 Hz), 4.69 ppm (dt, 2H, J=47.2 Hz, 4.9 Hz), 3.80 ppm (s, 3H), 3.52 ppm (dt, 2H, J=25.6 Hz, 4.9 Hz).

Example 4(iii): Ethyl 3-((2-chloro-5-methoxyphenyl)(2-fluoroethyl)amino)-2-oxocyclohexanecarboxylate

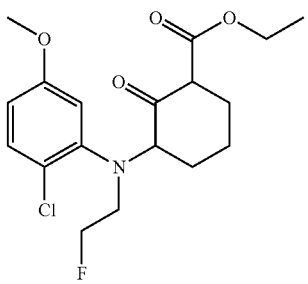 [SMILES: CCOC(=O)C1CCCC(N(CCF)c2cc(OC)ccc2Cl)C1=O]

2-chloro-N-(2-fluoroethyl)-5-methoxyaniline (3.86 g, 18.95 mmol) was dissolved in THF (90 ml) in a dry flask under argon and cooled to −40° C. Potassium hexamethyldisilazide (55.1 g, 276 mmol) dissolved in THF (45 ml) and added dropwise over 30 min while the temp was kept below −40° C. After 15 min a solution of ethyl 3-bromo-2-oxocyclohexanecarboxylate (29.9 g, 120 mmol) in THF (50 ml) was added over 50 min while the temp was kept below −40° C. After complete addition the cooling bath was removed and the mixture was stirred at ambient temperature for 4 h. Brine (65 ml) was added followed by 6M hydrochloric acid (20 ml, 120 mmol) while keeping the temperature at 20-25° C. Phases were separated and and the organic phase was evaporated to an oil and dissolved in ethyl acetate (50 ml). The aqueous phase was extracted with ethylacetate (50 ml) and the combined organic phases was washed with water (100 ml), dried over magnesium sulfate and evaporated to an oil. The crude product was used in the next step.

Example 4(iv): Ethyl 8-chloro-9-(2-fluoroethyl)-5-methoxy-2,3,4,9-tetrahydro-1H-carbazole-4-carboxylate

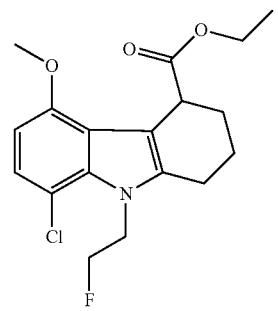 [SMILES: CCOC(=O)C1CCCc2c1c1c(OC)ccc(Cl)c1n2CCF]

The crude material from the previous step was dissolved in diethyl ether (120 ml) in a dry flask under argon. Zinc chloride (10.24 g, 75 mmol) was added and the mixture was refluxed overnight. The dark brown homogenous solution was cooled and 12% hydrochloric acid (60 ml, 237 mmol) was slowly added. The mixture was extracted with 3× ethyl acetate (50 ml) and the organic phase was washed with 3× water 50 ml. The organic phase was dried over MgSO$_4$ and evaporated to an oil. The crude product was purified silica (6×20 cm) with dichloromethane to yield 3.2 g of the title compound.

$^1$H NMR, 400 MHz (CDCl$_3$, 25° C.): 6.79 ppm (d, 1H, J=8.4 Hz), 6.19 ppm (d, 1H, J=8.4 Hz), 4.75-4.60 ppm (m, 2H), 4.52 ppm (dd, 1H, J=4.45 Hz, 5.45 Hz), 4.47-4.30 ppm (m, 1H), 4.03-3.92 ppm (m, 2H), 3.63 ppm (s, 3H), 2.64-2.47 ppm (m, 2H), 1.94-1.67 ppm (m, 5H), 1.08 ppm (t, 3H, J=7.1 Hz).

Example 4(v): Ethyl 9-(2-fluoroethyl)-5-methoxy-2,3,4,9-tetrahydro-1H-carbazole-4-carboxylate

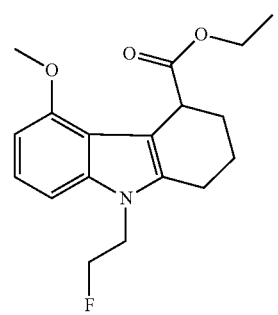 [SMILES: CCOC(=O)C1CCCc2c1c1c(OC)cccc1n2CCF]

Ethyl 8-chloro-9-(2-fluoroethyl)-5-methoxy-2,3,4,9-tetrahydro-1H-carbazole-4-carboxylate (3.2 g, 9.04 mmol) was dissolved in methanol (75 ml) and triethylamine (1.387 ml, 9.95 mmol). The flask was flushed with argon and palladium on carbon 10% (9.62 g, 9.04 mmol) was added. The flask was evacuated and flushed with hydrogen twice and then allowed to stir overnight fitted with a hydrogen filled balloon. The following day the mixture was filtered and evaporated to an oil. The oil was taken up in ethyl acetate and washed with water. The organic phase was dried over MgSO$_4$ and evaporated to an oil. The crude product was used in the next step.

$^1$H NMR, 400 MHz (CDCl$_3$, 25° C.): 7.03 ppm (t, 1H, J=8.0 Hz), 6.83 ppm (d, 1H, J=8.0 Hz), 6.45 ppm (d, 1H, J=8.0 Hz), 4.73-4.67 ppm (m, 1H), 4.61-4.55 ppm (m, 1H), 4.31 ppm (t, 1H, J=5.2 Hz), 4.25 ppm (t, 1H, 5.2 Hz), 4.16 ppm (q, 2H, J=7.1, 14.2 Hz), 4.1 ppm (t, 1H, J=5.6 Hz), 3.81 ppm (s, 3H), 2.79-2.61 ppm (m, 2H) 2.15-1.93 (m, 3H) 1.93-1.81 ppm (m, 1H) 1.24 pp (t, 3H, J=7.06 Hz).

Example 4(vi): 9-(2-fluoroethyl)-5-methoxy-2,3,4,9-tetrahydro-1H-carbazole-4-carboxylic acid

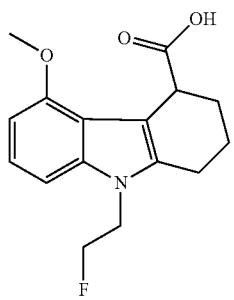 [SMILES: COc1cccc2c1c1c(n2CCF)CCCC1C(=O)O]

Ethyl 9-(2-fluoroethyl)-5-methoxy-2,3,4,9-tetrahydro-1H-carbazole-4-carboxylate (2.75 g, 8.61 mmol) was dissolved in ethanol (35 ml) and a solution of sodium hydroxide (4.13 g, 103 mmol) in water (20 ml) was added and the mixture was refluxed overnight. After evaporation of the ethanol the mixture was adjusted to pH 1 with hydrochloric acid under cooling. The slurry was extracted with ethyl acetate (2×50 ml), dried and evaporated to yield 2.25 g of the title compound. The crude product was used in the next step.

$^1$H NMR, 400 MHz (CDCl$_3$, 25° C.): 10 ppm (broad m, 1H), 7.09 ppm (t, 1H, J=8.0 Hz), 6.92 ppm (d, 1H, J=8.0 Hz), 6.57 ppm (d, 1H, J=8.0 Hz), 4.74-4.68 ppm (m, 1H), 4.62-4.56 ppm (m, 1H), 4.33 ppm (t, 1H, J=5.2 Hz), 4.27 ppm (t, 1H, J=5.2 Hz), 4.18-4.12 ppm (m, 1H), 3.96 ppm (s, 3H), 2.85-2.59 ppm (m, 2H) 2.39-2.29 (m, 1H) 2.29-2.14 ppm (m, 1H) 2.06-1.93 (m, 1H), 1.90-1.77 (m, 1H).

Example 4(vii): 9-(2-fluoroethyl)-5-methoxy-2,3,4,9-tetrahydro-1H-carbazole-4-carbonyl chloride

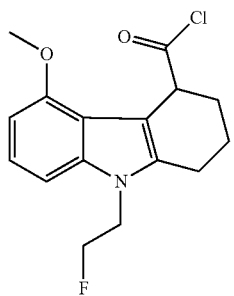

9-(2-fluoroethyl)-5-methoxy-2,3,4,9-tetrahydro-1H-carbazole-4-carboxylic acid (2 g, 6.87 mmol) was suspended in dichloromethane (25 ml, 389 mmol) and oxalylchloride (1.803 ml, 20.60 mmol) was added under argon. The dark solution was stirred for 1.5 h at ambient temperature and then evaporated to a brown foam. The crude product was used in the next step.

Example 4(viii): N-benzyl-N-ethyl-9-(2-fluoroethyl)-5-methoxy-2,3,4,9-tetrahydro-1H-carbazole-4-carboxamide

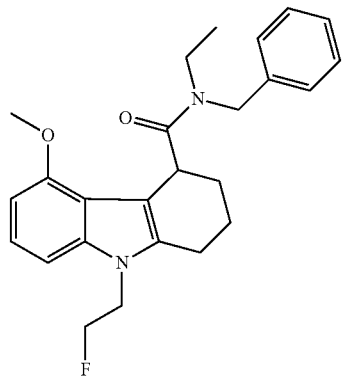 [SMILES: CCN(Cc1ccccc1)C(=O)C1CCCc2c1c1c(OC)cccc1n2CCF]

9-(2-fluoroethyl)-5-methoxy-2,3,4,9-tetrahydro-1H-carbazole-4-carbonyl chloride (532 mg, 1.716 mmol) was dissolved in dichloromethane (4 ml) and N-ethylbenzylamine (696 mg, 5.15 mmol) was added dropwise. The mixture was stirred overnight and worked up with diluted hydrochloric acid/DCM and water/DCM. The organic phase was dried and evaporated and the resulting solid was dissolved in ethanol (25 ml) and left overnight. The formed crystalline precipitate was collected and dried to yield 470 mg of the racemate.

$^1$H NMR, 400 MHz (CDCl$_3$, 25° C.): 7.44-7.22 ppm (broad m, 5H), 7.04 ppm (t, 1H, J=8.0 Hz), 6.86 ppm (d, 1H, J=8.0 Hz), 6.47 ppm (dd, 1H, J=8.0 Hz, 8.0 Hz), 4.96-4.52 ppm (m, 5H), 4.38-4.23 ppm (m, 2H), 3.90-3.22 ppm (m, 5H), 2.91-2.58 ppm (m, 2H), 2.35-1.72 ppm (m, 4H), 1.33 ppm (t, 2.2H, J=7.2 Hz), 1.15 ppm (t, 0.8H, J=7.2 Hz).

The S-enantiomer is obtained using known enantiomeric separation techniques, e.g. SFC.

Example 5: Synthesis of (S)—N-methyl-N-isopropyl-9-(2-fluoroethyl)-5-methoxy-2,3,4,9-tetrahydro-1H-carbazole-4-carboxamide (Non Radioactive Compound 4 of the Invention)

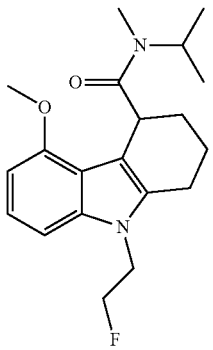 [SMILES: COc1cccc2c1c1c(n2CCF)CCCC1C(=O)N(C)C(C)C]

Steps 4(i)-(vii) as described above were carried out and then 9-(2-fluoroethyl)-5-methoxy-2,3,4,9-tetrahydro-1H-carbazole-4-carbonyl chloride (0.532 g, 1.716 mmol) was dissolved in dichloromethane (4 ml) and N-methyl-isopropylamine (0.449 g, 5.15 mmol) was added dropwise. The mixture was stirred overnight and worked up with diluted hydrochloric acid/DCM and water/DCM. The organic phase was dried and evaporated and the resulting solid was dissolved in ethanol (25 ml) and left overnight. The formed crystalline precipitate was collected and dried to yield 285 mg of the racemate.

$^1$H NMR, 400 MHz (CDCl$_3$, 25° C.): 6.92 ppm (t, 1H, J=8.0 Hz), 6.75 ppm (d, 1H, J=8.0 Hz), 6.36 ppm (dd, 1H, J=8.0 Hz, 8.0 Hz), 4.70-4.13 ppm (m, 6H), 3.71 ppm (s, 3H), 3.61 ppm (q, 2H, J=7.2), 3.58-3.47 ppm (m, 0.5H), 3.36-3.11 ppm (m, 1.5H), 2.77-2.52 ppm (m, 2H), 2.23-1.55 ppm (m, 5H) 1.32-1.24 (m, 3H), 1.19-1.06 (m, 6H).

The S-enantiomer is obtained using known enantiomeric separation techniques, e.g. SFC.

Example 6: Binder/Non-Binder Assay of Racemates

Membrane protein was prepared from human platelets obtained from 4 donor whole blood samples. Two of these donor samples were previously identified as having high affinity and 2 identified as having low affinity based on PBR28 binding affinity. Platelet pellets were homogenised in 10 ml buffer 1 (0.32 mM sucrose, 5 mM Tris base, 1 mM MgCl$_2$, pH 7.4, 4° C.). The homogenates were centrifuged at 48,000×g for 15 minutes at 4° C. in a Beckman J2-MC centrifuge. The supernatant was removed and pellets were re-suspended in at least 10 ml buffer 2 (50 mM Tris base, 1 mM MgCl$_2$, pH 7.4, 4° C.) and washed by centrifugation at 48,000×g for 15 min at 4° C. in buffer 2. Membranes were suspended in 2 ml buffer 2 and the protein concentration was determined using Protein Assay Kit II (Bio Rad cat #500-0002). Aliquots were stored at −80° C. until use.

Aliquots of membrane suspension were thawed and homogenised with assay buffer 3 (50 mM Tris base, 140 mM NaCl, 1.5 mM MgCl$_2$, 5 mM KCl, 1.5 mM CaCl$_2$, pH 7.4, 37° C.). For competitive binding experiments, non-labelled PBR28 (ABX cat #1653) or PK11195 was diluted on a Beckman Biomek 2000 workstation at 11 serial dilutions ranging from 100 μM to 1 nM and added to a non-binding 96 well microplate containing 5 nM [$^3$H]PK11195 (Perkin Elmer Cat # NET885001 MC). Non-radioactive Compound 1 was diluted on a Beckman Biomek 2000 workstation at 11 serial dilutions ranging from 1 μM to 0.01 nM. GE180 and non-radioactive Compound 2 were diluted at 11 serial dilutions ranging from 100 μM to 1 nM. Total and nonspecific binding assessments were also performed. 160 μL of platelet membranes diluted to 30 μg/mL were added to the assay plate for a final volume of 200 μL/well. Assay plates were incubated at 37° C. for at least one hour with termination of incubation by filtering onto GF/B glass fibre plates (Perkin Elmer; cat #6005177) pre-soaked in 0.1% PEI in saline for 60 minutes. Assay plates were rinsed five to six times with ice cold buffer 4 (50 mM Tris Base, 1.4 mM MgCl$_2$, pH 7.4, 4° C.) on a Perkin Elmer Filtermate 196. Plates were then dried, the bottoms sealed, and 50 μL of MicroScint 20 (Perkin Elmer cat #6013621) was added to each well. After sealing the tops, the plates were allowed to equilibrate for at least 30 minutes and the captured radioactivity was counted on a Perkin Elmer TopCount NTX. Compound 1 and Compound 2 were used as racemates. All the compounds were tested in triplicate in this [$^3$H]PK11195 competitive binding assay and the affinity of the compounds was determined by analysing the data using GraphPad Prism 5.0 and the low:high affinity ratios were calculated.

| Compound | Low Affinity Site (nM) | High Affinity Site (nM) | Low:High |
|---|---|---|---|
| GE180 | 37.87 | 2.45 | 15.44 |
| Compound 1 | 5.98 | 1.85 | 3.24 |
| Compound 2 | 44.86 | 43.82 | 1.02 |

Example 7: Binder/Non-Binder Assay for Resolved Enantiomers

Compound 1 and Compound 2 were resolved into enantiomers and the competitive binding assay was performed using platelets isolated from the same 4 human donor whole blood samples as described in Example 6. The same assay procedure as Example 6 was followed for the competitive binding assay and compounds the prior art compounds PK11195, PBR28 and GE180 along with the resolved enantiomers of Compounds 1 and 2 of the invention were used at 11 serial dilutions ranging from 100 μM to 1 nM. All the compounds were tested in triplicate in the [$^3$H]PK11195 competitive binding assay and the affinity of the compounds was determined by analysing the data using GraphPad Prism 5.0 and the low:high affinity ratios were calculated.

| Compound | Low Affinity Site (nM) | High Affinity Site (nM) | Low:High |
|---|---|---|---|
| PK11195 (Prior Art) | 6 | 4 | 1 |
| PBR28 (Prior Art) | 117 | 4 | 28 |
| GE180 (Prior Art) | 23 | 7 | 3 |
| Compound 1 E1 | 5 | 4 | 1 |
| Compound 1 E2 | 125 | 4 | 32 |
| Compound 2 E1 | 23 | 24 | 1 |
| Compound 2 E2 | 402 | 83 | 5 |

E1 = S enantiomer and
E2 = R enantiomer

The invention claimed is:
1. A compound of Formula I:

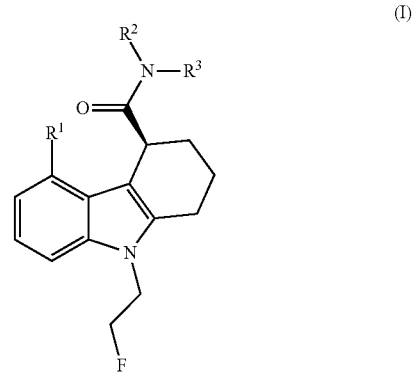

(I)

wherein:
R$^1$ is hydrogen or methoxy;
R$^2$ is ethyl and R$^3$ is benzyl, or R$^2$ is methyl and R$^3$ is isopropyl, and
F is $^{18}$F.

2. The compound as defined in claim 1, wherein R¹ is methoxy.

3. The compound as defined in claim 1, wherein R¹ is hydrogen.

4. The compound as defined in claim 1, wherein R² is ethyl and R³ is benzyl.

5. The compound as defined in claim 1, wherein R² is methyl and R³ is isopropyl.

6. A precursor compound for use in the preparation of the compound of Formula I, wherein said precursor compound is of Formula II:

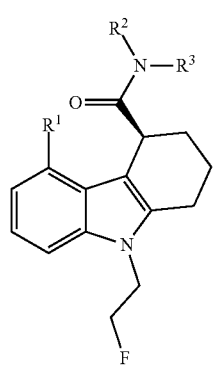

(I)

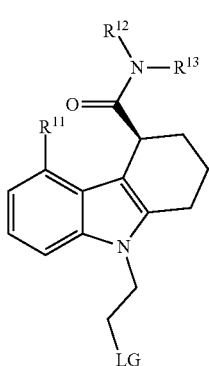

(II)

wherein
R¹ is hydrogen or methoxy;
R² is ethyl and R³ is benzyl, or R² is methyl and R³ is isopropyl;
R¹¹, R¹² and R¹³ are as defined for R, R² and R³ in Formula I; and
LG is a leaving group.

7. The precursor compound as defined in claim 6, wherein LG is chloro, bromo, iodo, tosylate (OTs), nosylate (ONs), mesylate (OMs), or triflate (OTf).

8. A method to prepare the compound of Formula I as defined in claim 1, the method comprising reacting a precursor compound of Formula II with a suitable source of [¹⁸F]fluoride to obtain said compound of Formula I,

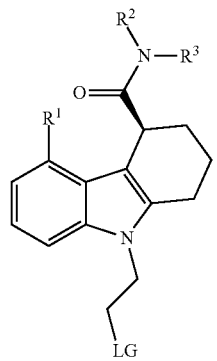

(II)

wherein
R¹¹ is hydrogen or methoxy;
R¹² is ethyl and R¹³ is benzyl, or R¹² is methyl and R¹³ is isopropyl; and
LG is a leaving group.

9. The method as defined in claim 8 which is automated.

10. A cassette for carrying out the method as defined in claim 9, the cassette comprising:
(i) a vessel containing the precursor compound of Formula II; and,
(ii) means for eluting the vessel of step (i) with a suitable source of [¹⁸F]fluoride.

11. A radiopharmaceutical composition comprising the compound of Formula I as defined in claim 1 together with a biocompatible carrier in a form suitable for mammalian administration.

12. An in vivo imaging method for determining the distribution and/or the extent of translocator protein (TSPO) expression in a subject, the method comprising:
(i) administering to said subject a compound of Formula I;
(ii) allowing said compound to bind to TSPO expressed in said subject;
(iii) detecting signals emitted by the radioisotope of said compound using positron-emission tomography (PET);
(iv) generating an image representative of the location and/or amount of said signals; and,
(v) determining the distribution and extent of TSPO expression in said subject wherein said expression is directly correlated with said signals emitted by said compound,
wherein the compound of formula I is:

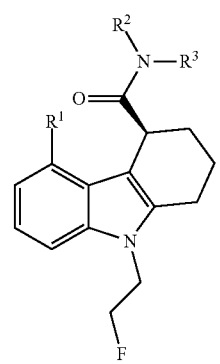

(I)

wherein:

$R^1$ is hydrogen or methoxy;

$R^2$ is ethyl and $R^3$ is benzyl, or $R^2$ is methyl and $R^3$ is isopropyl, and F is $^{18}$F.

13. The in vivo imaging method as defined in claim 12 which is carried out repeatedly during the course of a treatment regimen for said subject, said regimen comprising administration of a drug to combat a TSPO condition.

* * * * *